(12) United States Patent
Kerschmann

(10) Patent No.: US 6,372,512 B1
(45) Date of Patent: Apr. 16, 2002

(54) COMBINED EN BLOC STAINING AND EMBEDDING PROCESS

(75) Inventor: Russell L. Kerschmann, San Francisco, CA (US)

(73) Assignee: Resolution Sciences Corporation, Corte Madera, CA (US)

(*) Notice: Subject to any disclaimer, the term of this patent is extended or adjusted under 35 U.S.C. 154(b) by 0 days.

(21) Appl. No.: 09/154,430

(22) Filed: Sep. 16, 1998

(51) Int. Cl.[7] .................................................. G01N 1/30
(52) U.S. Cl. ........................ 436/174; 436/172; 435/40.5; 435/40.52
(58) Field of Search ........................... 436/63, 172, 177, 436/174; 435/40.5, 40.52

(56) References Cited

U.S. PATENT DOCUMENTS

| | | | |
|---|---|---|---|
| 3,997,656 A | * 12/1976 | Wertlake | 424/3 |
| 4,497,792 A | * 2/1985 | Gindler | 424/3 |
| 4,588,579 A | * 5/1986 | Bachhuber | 424/3 |
| 4,960,330 A | * 10/1990 | Kerschmann | 356/36 |
| 5,208,148 A | 5/1993 | Haughland et al. | |
| 5,442,045 A | 8/1995 | Haughland et al. | |
| 5,451,663 A | 9/1995 | Kang et al. | |
| 5,616,502 A | 4/1997 | Haughland et al. | |
| 5,648,270 A | 7/1997 | Kuhn et al. | |
| 5,658,751 A | 8/1997 | Yue et al. | |
| 5,696,157 A | 12/1997 | Wang et al. | |

OTHER PUBLICATIONS

Carson, Freida L., "Fixation," pp 1–42. In Histotechnology, *American Society of Clinical Pathologists* 2nd Ed. Chicago, (1997).

Prophet, Edna B., "Fixation," pp 25–43. In Laboratory methods in histotechnology (Prophet, Mills, Arrington, Sobin), *Armed Forces Institute of Pathology*, Washington, (1994).

Sheehan and Hrapchak, "Fixation," pp 40–78. In Theory and practice of histotechnology, *Battelle Memorial Institute* (2nd Ed.), Battelle Press, Columbus, (1980).

Wehry, Earl L., "Effects of molecular environment on fluorescence and phosphorescence," pp 127–184, *In Practical fluorescence* 2nd Ed., (Guilbault), Marcel Dekker, Inc., New York, (1990).

* cited by examiner

*Primary Examiner*—Lyle A. Alexander
(74) *Attorney, Agent, or Firm*—Clark & Elbing LLP

(57) ABSTRACT

A method for preparing an organic sample for cutting and subsequent examination, involving immersing the sample in a composition containing: an infiltrating substance; an embedding substance, which can be the same or different from the infiltrating substance; and a stain that chemically associates with the organic sample, wherein the stain exhibits different detectable properties when associated and not associated with the sample.

7 Claims, No Drawings

COMBINED EN BLOC STAINING AND EMBEDDING PROCESS

BACKGROUND OF THE INVENTION

In present day practice the preparation of organic tissue samples and other material for transmission microscopy, both visible light and electron microscopy, is normally carried out by subjecting the sample to a series of chemical treatments culminating in the production of a solid block in which the sample is embedded. This operation is normally carried out automatically in commercial tissue processors, which are complicated mechanical devices with elaborate temperature control and fluid delivery systems. Their complexity makes them expensive and demanding of frequent technical attention and maintenance. Furthermore, standard tissue processing devices are large and stationary, not portable.

In the conventional tissue preparation process, the tissue is first chemically fixed with formalin, glutaraldehyde, or other materials which serve to preserve the sample from autolysis (self-degradation), and to render the sample rigid as well as to increase its permeability, thereby enhancing the infiltration of subsequent solutions. The infiltration steps which follow are designed to remove all of the water from the sample through progressive replacement with increasing concentrations of solvents such as alcohol and xylene. In the case of conventional light microscopy, infiltration is followed by treatment with melted paraffin, and then the sample is cooled to room temperature whereupon it solidifies. The hardened, infiltrated tissue is then positioned in a mold and surrounded by additional paraffin to produce a tissue block. Microwave ovens have been employed in histology laboratories to speed the penetration of various substances.

In addition to paraffin, plastic is widely employed for producing tissue blocks. The plastic may be methacrylate, epoxy polymer, or related material, but in any case the tissue is subjected to a process roughly similar to that employed in paraffin processing. The water in the tissue is replaced by organic solvents, which are then replaced by liquid polymer. In the case of methacrylate and other water soluble polymers, the dehydration process may be greatly shortened or eliminated. Often the infiltration of the sample by plastic takes place in a small container which also serves as the embedding mold with an excess of polymer that both infiltrates and surrounds the sample, thus infiltration and embedment are combined. The mixed precursor components of the polymer are made to solidify (polymerize) by various means, including exposure to ultraviolet light, heat, or by addition of a chemical catalyst. Plastic processing has been adopted for both light and electron microscopy.

Alternatively, in the frozen section method, fresh unfixed tissue is immediately embedded in a clear, water-soluble, semisolid medium such as O.C.T. compound (Miles, Inc., Elkhart, Ill.) and quickly frozen. This technique is performed to preserve certain tissue components that may be sensitive to extremes of temperature and chemical environment (e.g. antigens) or in the case where microscopic examination of tissue must be accomplished rapidly, such as during some types of cancer surgery. Unlike the "permanent" techniques discussed above, in the frozen section method water is not first extracted from the tissue but instead remains to be frozen along with the encasing embedding medium to form a solid block. The timing of this operation leaves little opportunity for the infiltration/embedding medium to infiltrate the tissue, and so normally the medium serves purely a supportive function.

In conventional optical and electron microscopy, after the block is produced, thin sections of the sample with the surrounding embedding material are cut from the block and transferred to glass slides or other support. The tissue section is then stained with any of a variety of colored or fluorescent dyes for examination. In some techniques the embedding material is chemically removed prior to staining.

Alternatively, methods have been introduced for en bloc staining, wherein the entire sample is stained by immersion prior to being subjected to infiltration and embedment. Sections are then cut from the block for transmission microscopy, or the cut face of the block itself is imaged.

While in some cases the infiltration and embedment steps have been combined, the staining of the tissue has always been implemented separately.

SUMMARY OF THE INVENTION

In general, the invention features a method for preparing an organic sample, e.g., a biological tissue sample, for cutting and subsequent examination; the method involves combining histologic staining, infiltration, and embedding into a single step. Thus, according to the invention, the sample is immersed in a composition composed of: (a) an infiltrating substance; (b) an embedding substance, which can be the same or different from the infiltrating substance; and (c) a stain that chemically associates with the organic sample, and which exhibits different detectable properties when associated and when not associated with the sample. Prior to immersion in the composition, the sample, if it is not a frozen section, preferably is treated with a chemical fixative.

The process preferably employs environmentally sensitive fluorescent stains or dyes that express a specified color or colors (i.e., wavelength) upon being chemically bound to or associated with the sample, but do not express the same specified color or colors when mixed with the embedding medium in the absence of the sample, or express no color when not associated with the sample. This makes it possible to clearly distinguish the tissue or other sample material embedded in the block from the embedding material itself.

As used herein, the term "chemical fixative" refers to a chemical solution that preserves, permeabilizes and aids in hardening the sample. "Infiltrating substance" refers to a liquid or series of liquids that penetrate throughout the tissue to the molecular level and are then transformed into a solid in order to render the sample rigid. "Embedding" or "embedment" refers to positioning the infiltrated tissue in a mold and surrounding it with a substance (usually the same as the infiltrating substance) which is then hardened to form an encasing block. The embedding substance thus serves to provide rigid support and to facilitate the cutting process. "Sectioning" refers to cutting from the block thin slices which may then be mounted on glass slides or other support. "Staining" refers to treating tissue with a colored (including flourescent) substance that associates with the tissue on the molecular level.

Use of conventional, non-environmentally sensitive stains or dyes admixed with the infiltration and embedding medium would cause the embedding medium to express a color or colors similar to that expressed by the tissue, resulting in a loss of contrast between the sample and the infiltration/embedding medium.

The combination of the stain with the infiltration/embedding material reduces the number of steps required to produce embedded tissue for microscopic examination. The invention thus makes possible the production of less complex and expensive automated tissue processing devices. The invention also makes possible, for the first time, a truly portable histopathology laboratory. For example, a compact, field-rated instrument such as is made possible by the invention would find widespread use in military field hospitals, environmental science studies, epidemiology projects, and other special environments such as spacecraft. In civilian medicine, such a device can be incorporated into small satellite laboratories, such as those presently operating within physicians' offices. In this setting they would reduce the expense and turnaround time for the delivery of clinical diagnoses and make a major impact on the overall cost of medicine.

When combined with an automated block sectioning and image acquisition system such as the Surface Imaging Microscope (U.S. Pat. No. 4,960,330, hereby incorporated by reference), the resultant comprehensive system will accept a biopsy as delivered to a histology laboratory (in which the biopsy usually will have been treated with a fixative) and generate a diagnostic-quality image without intervening human labor. This will greatly reduce the cost and delay involved in obtaining a histopathologic diagnosis.

Another aspect of the invention features a frozen section tissue preparation method in which freezing is postponed for a period of time between about three and sixty minutes past conventional freezing time (i.e., beyond immediate freezing) so that infiltration into the tissue by the medium will occur, making a combined stain/infiltration/embedment process possible.

Other features and advantages of the invention will be apparent from the following description of the preferred embodiments thereof, and from the claims.

DETAILED DESCRIPTION

As is mentioned above, the invention employs several components, now discussed in greater detail.
Dyes (Stains)

The invention employs dyes which are classified as "environmentally sensitive," or "metachromatic."

Environmentally sensitive dyes constitute a subset of histochemical stains, many of which are fluorescent. Like most fluorochromes, these compounds absorb light of a specific wavelength and reemit it at a longer wavelength or wavelengths. The spectral properties of environmentally sensitive dyes are strongly influenced by their proximity to target molecules, such that their emission wavelength is altered. Thus, these dyes change colors when they combine with certain types of materials. In some cases, the environmentally sensitive dye may emit light only when bound to its target, and is otherwise not visible.

Environmental sensitivity can be imparted by a variety of chemical mechanisms. It is frequently displayed by the analine dyes upon binding to polyanions, during which the dye may undergo various states of polymerization which significantly alter its optical properties. The commonly used stain acridine orange can express as many as three different colors, depending on the type of molecule to which it becomes bound. Acridine orange is one of a group of nucleic acid-specific stains, many of which are poorly flourescent when not bound to DNA or RNA, and are therefore relatively environmentally sensitive. Other examples are DAPI (4',6-diamidino-2phynlindole) and the Hoechst dyes 33258 and 33342.

Alternatively, the covalent structure of the dye itself may be altered: for example, attachment of benzoxadiazole derivatives to thiol groups on certain target compounds produces thioethers which display shorter absorption and emission wavelengths than do free dye molecules. Pyrene maleimide and the bromobimane-related stains are examples of compounds that show little fluorescence in the unbound state, but display active emission when bonded to thiol groups present in abundance in many proteins.

The color of a fluorochrome dye may be exquisitely sensitive to the polarity of the environment, such that a dye molecule attached to a hydrophobic region of a protein will display a detectable different color than one present in a more hydrophilic region of the target. Polar sensitivity is seen with the dyes acrylodan and badan, as well as with the popular environmentally sensitive dye PRODAN (6-Propionyl-2-dimethylaminonaphthalene) from which they are derived.

Environmental sensitivity also may result from the proximity of one fluorochrome dye to a second through the phenomenon of fluorescence resonance energy transfer. Individual dye molecules positioned close to one another on a target molecule (approximately 50 Angstroms) will interact energetically, altering their emission characteristics. This effect has been used as a sensitive tool to measure atomic scale distances, for example in muscle research.

Many suitable environmentally sensitive dyes are available from Molecular Probes, Inc., Eugene, Oreg.; the dyes and catalogs are available by telephone: (800) 438-2209. Most of these dyes are the subject of issued U.S. patents, all of which are hereby incorporated by reference. The Molecular Probes environmentally-sensitive dyes, which tend to label proteins, are cataloged as falling into the following three categories: bezoxadiazole derivatives, napthalene derivatives, and pyrene derivatives.
Infiltration/Embedding Media The infiltration and embedding media (which usually are, but need not be, one substance) must be compatible with the stain and its mechanism of action. Because the environmentally-sensitive stains used in the invention are hydrophilic dyes that must penetrate and chemically associate with the sample, the infiltrating/embedding media also must be water-miscible. Water-insoluble polymers, such as are used in some histology applications, are unacceptable because they do not permit miscibility of the dye with the medium, which is required for a one-step formulation. Further, the infiltration/embedding media should not quench (suppress the fluorescence emission of) dye that is bound to the tissue. All of these compatibility issues can be readily and routinely resolved by simply mixing combinations of components and observing the result.

Examples of suitable hydrophilic infiltrating/embedding polymers, and their method of preparation and use, are given in Carson, id. Some suitable media are water-soluble waxes such as Carbowax (Union Carbide Corp., Danbury, Conn.), glycol methacrylate, and agar/gelatin.

Generally, the components in the one-step composition of the invention are mixed in one of two ways: (1) the components are added to a mixing vessel, mixed, and then poured into the mold containing the sample, or (2) the components are mixed in the mold, just prior to adding the sample. Mixing is carried out in any conventional manner.

EXAMPLES

The following examples are not intended to be limiting to the scope of the claims.

Example 1

A one-step tissue preparation composition where proteins in the sample are to be stained contains the following components:

Dye: Molecular Probes monobromobimane stain; final concentration in formula 0.02%. Embedding/infiltration medium: Full strength glycol methacrylate catalyzed infiltration resin (JB-4, Polysciences, Inc., Warrington, Pa.).

The above components are gently mixed in a 100 ml. brown glass vessel at room temperature for 60 minutes. Tissue samples are placed in the formulation in individual 10 cc vials and mixed by rotation for 24 hours at 4° C. The infiltrated and stained samples are then transferred to 2 ml embedding capsules with an excess of formulation, centrifuged at 5,000 rpm for 10 minutes to facilitate settling of the sample, and allowed to polymerize at room temperature (approximately 1 hour). Sections are cut from the hardened blocks on a microtome, mounted on glass slides, and examined under fluorescence microscopy.

Example 2

A one-step tissue preparation composition, where nucleic acids in the sample are to be stained, contains the following components:

Dye: Acridine orange, final concentration in formula 0.05%. Infiltration/embedding medium: Carbowax.

The components are mixed by gentle stirring in a 100 ml. brown glass vessel at 56° C. to 58° C. for 60 minutes. Maintaining these conditions, tissue samples are placed in the formulation and mixed by slow rotation for 6 hours. The infiltrated and stained samples are then transferred to embedding molds, and allowed to solidify on a cooling plate. Sections are cut from the blocks on a microtome, mounted on glass slides, and imaged by computerized fluorescence microscopy. The images are subjected to digital filtering which removes all non-nucleic acid signals based upon the differential coloration properties of the stain, including removing any signal originating from the medium. Alternatively, the Carbowax has been previously opacified by the addition of absorbent dyes and the cut face of the block surface is imaged, obviating glass slides (as in U.S. Pat. No. 4,960,330.).

Example 3

A one-step tissue preparation composition, where general tissue elements in the sample are to be stained for interoperative diagnosis, contains the following components:

Dyes: DAPI (4',6-diamidino-2phenylindole) at a final concentration in the formula of 0.2% (to stain nucleic acids); combined with 0.1% pyrene maleimide at a final concentration of 0.1% (to stain proteins). Infiltration/embedding medium: O.C.T. compound.

A formulation is prepared by combining the components and gently stirring in a 100 ml. brown glass vessel at room temperature for 1 hour. Fresh tissue samples are taken directly from the patient, placed in an excess of the formulation, and mixed for 30 minutes under slow rotation in a laboratory microwave unit to facilitate penetration. The infiltrated and stained samples are then positioned on metal chucks and surrounded with additional formulation before being placed in a −20° C. freezer. The resulting frozen blocks are sectioned in a cryostat microtome and mounted on glass slides for interoperative diagnosis by digital fluorescence microscopy.

What is claimed is:

1. A method for preparing an organic sample for cutting and subsequent examination, said method comprising immersing said sample in a composition comprising:
    an infiltrating substance;
    an embedding substance, which can be the same or different from the infiltrating substance; and
    a stain that chemically associates with the organic sample, wherein the stain exhibits different detectable properties when associated and not associated with the sample.

2. The method of claim 1, wherein the infiltrating and embedding substances are the same substance.

3. The method of claim 1, wherein the stain exhibits different colors or fluorescence wavelength when associated and when not associated with the sample, or exhibits a detectable color or wavelength only when associated with the sample.

4. The method of claim 1, wherein the sample comprises biological tissue.

5. The method of claim 3, wherein the stain fluoresces at a predetermined wavelength when chemically associated with the sample, and does not substantially so fluoresce when not associated with the sample.

6. A histology composition useful for preparing an organic sample for cutting and subsequent examination, said composition comprising:
    an infiltrating substance;
    an embedding substance, which can be the same or different from the infiltrating substance; and
    a stain that chemically associates with the organic sample, wherein the stain exhibits different detectable properties when associated and not associated with the sample.

7. A method for preparing an organic sample for cutting and subsequent examination, said method comprising:
    a) immersing said sample in a composition comprising:
        an infiltrating substance;
        an embedding substance, which can be the same or different from the infiltrating substance; and
        a stain that chemically associates with the organic sample, wherein the stain exhibits different detectable properties when associated and not associated with the sample; and then
    b) freezing said sample.

* * * * *